United States Patent [19]
Fujii et al.

[11] Patent Number: 6,060,626
[45] Date of Patent: May 9, 2000

[54] FLUORINE-CONTAINING ETHER COMPOUND

[75] Inventors: Yasuyuki Fujii; Eiko Tamura; Shinji Yano; Hisakazu Furugaki, all of Wakayama, Japan

[73] Assignee: Kao Corporation, Tokyo, Japan

[21] Appl. No.: 09/057,447

[22] Filed: Apr. 9, 1998

[30] Foreign Application Priority Data

Oct. 16, 1997 [JP] Japan .................................. 9-283649

[51] Int. Cl.[7] ................................................ C07C 45/00
[52] U.S. Cl. .......................................... 568/463; 568/463
[58] Field of Search ............................................ 568/463

[56] References Cited

FOREIGN PATENT DOCUMENTS 0 753 500   1/1997   European Pat. Off. .
6-227942    8/1994   Japan .

OTHER PUBLICATIONS

Chemical Abstracts, vol. 110: 164022z, 1989.
Chemical Abstracts, vol. 108: 149,998n, 1988.

Primary Examiner—James O. Wilson
Attorney, Agent, or Firm—Oblon, Spivak, McClelland, Maier & Neustadt, P.C.

[57] ABSTRACT

A novel fluorine-containing compound having functions corresponding to those of fluorine is provided, which is stable under various conditions, excellent in compatibility with other solvents, and can be widely utilized as solvents, cosmetics, detergents, emulsifiers, surface finishing agents, lubricants, as well as lubricants or oils in the field of semiconductor/electronics.

That is, the present invention provides fluorine-containing ether compounds represented by the general formula (1):

$$Rf-(CH_2)_n-O-R^1 \qquad (1)$$

(wherein, Rf represents a straight or branched $C_{1-20}$ perfluoroalkyl or fluoroalkyl group, $R^1$ represents a straight or branched $C_{3-9}$ alkyl or a $C_{3-9}$ cycloalkyl group, n is a number from 1 to 8).

11 Claims, No Drawings

FLUORINE-CONTAINING ETHER COMPOUND

FIELD OF THE INVENTION

This invention relates to a novel fluorine-containing ether compound. More particularly, it relates to a novel fluorine-containing ether compound which can be widely utilized as solvents, cosmetics, detergents, emulsifiers, surface finishing agents, lubricants, as well as lubricants or oils in the field of semiconductor/electronics, etc.

DESCRIPTION OF PRIOR ART

Formerly, as general liquid lubricants used as oils for cosmetics, detergents, lubricants, etc., animal and vegetable or chemically synthesized esters (e.g., oils and fats) and hydrocarbons are known.

Desirable properties of such general liquid oils include, for example;

(1) having no smell and color;
(2) exhibiting no change in color and odor with time;
(3) excellent in touch;
(4) having appropriately low viscosity.

However, esters are not preferable because they may be hydrolyzed upon contact with water and have oily touch, while hydrocarbons are also undesirable because most of them have multi-branched structures, resulting in high viscosity although they are excellent in stability. Accordingly, none of the conventionally known liquid oils satisfy all of the above properties.

On the other hand, fluorine-containing organic compounds are known as oils for cosmetics, detergents, lubricants, etc. because they retain functions corresponding to those of fluorine, for example, water and oil repellency, low water absorption properties, electrical insulation properties, etc. Among them, for example, those having ester linkages have problems in hydrolysis resistance and those having polyoxyalkylene chain and perfluoropolyethers wherein all hydrogen atoms are substituted with fluorine atoms have problems in compatibility with other solvents, etc.

Accordingly, the object of the present invention is to provide novel fluorine-containing compounds which have functions of fluorine, and is stable under various conditions, and excellent in compatibility with other solvents, etc., and can be widely used as solvents, cosmetics, detergents, emulsifiers, surface finishing agents, lubricants, as well as lubricants or oils in the field of semiconductor/electronics.

JP-A 6-227942 describes fluorine-containing ether compounds such as decyl{2-(perfluorooctyl)ethyl}ether.

Although decyl{2-(perfluorooctyl)ethyl}ether has compatibility with hydrocarbon oil, ester oil and silicone oil etc., It has a problem that decyl{2-(perfluorooctyl)ethyl}ether has only a poor compatibility with fluorine oil.

DISCLOSURE OF THE INVENTION (Compounds)

The present inventors have studied intensively to solve the above problems, and as the results, we have found novel fluorine-containing ether compounds and have attained the present invention.

That is, the present invention provides fluorine-containing ether compounds represented by the general formula (1):

$$Rf-(CH_2)_n-O-R^1 \tag{1}$$

wherein, Rf represents a straight or branched $C_{1-20}$ perfluoroalkyl or fluoroalkyl group, $R^1$ represents a straight or branched $C_{3-9}$ alkyl or a $C_{3-9}$ cycloalkyl group, n is a number from 1 to 8.

The aspect of the preset invention, i.e., compounds of the present invention will be illustrated in detail.

In the fluorine-containing ether compounds of the present invention represented by the above general formula (1), Rf represents a straight or branched $C_{1-20}$ perfluoroalkyl or fluoroalkyl group, preferably, a straight or branched $C_{2-14}$ perfluoroalkyl group, particularly, a straight or branched $C_{4-12}$ perfluoroalkyl or fluoroalkyl group. $R^1$ represents a straight or branched $C_{3-9}$ alkyl or a $C_{3-9}$ cycloalkyl group, preferably a straight or branched $C_{6-9}$ alkyl group. Particularly, branched $C_{6-9}$ alkyl groups are preferable because of excellent compatibility or emulsifying ability with other solvents. n represents a number from 1 to 8, preferably 1 to 6, more preferably, 1 to 4, and particularly preferably 2.

Rf of the formula (1) may be a perfluoroalkyl group or a fluoroalkyl group in which at least one hydrogen atom has been substituted by a fluorine atom. A mixture of both may be included in the invention.

(Manufacturing Process)

The fluorine-containing ether compounds of the present invention represented by the above general formula (1) can be produced by reacting a fluorine-containing hydroxy compounds represented by the general formula (2):

$$Rf-(CH_2)_n-O-H \tag{2}$$

(wherein, Rf and n are the same as defined above) with carbonyl compound of the general formula (3):

(wherein $R^2$ and $R^3$ are the same or different to represent hydrogen atoms or $C_{1-9}$ alkyl groups, or $R^2$ and $R^3$ together may form a ring, provided that total carbon numbers of $R^2$ and $R^3$ should be 2 to 8) or polymer thereof in the presence of a catalyst in an atmosphere of hydrogen or in hydrogen gas.

Fluorine-containing hydroxy compounds represented by the general formula (2) include, for example, $C_{1-8}$ straight-chain alcohols having a perfluoroalkyl group or a fluoroalkyl group wherein at least one hydrogen atom of a $C_{1-20}$ straight or branched alkyl group is substituted by a fluorine atom. Embodiments include, but are not limited to, straight fluorine-containing alcohols such as 2,2,3,3,3-pentafluoropropanol, 2-(perfluorohexyl)ethanol, 2-(perfluorooctyl)ethanol, 2-(perfluorodecyl)ethanol, 6-(perfluoroethyl)hexanol, 6-(perfluorobutyl)hexanol, 6-(perfluorohexyl)hexanol, 6-(perfluorooctyl)hexanol, 2,2,3,4,4,4-hexafluorobutanol, 2,2,3,3-tetrafluoropropanol, 1H,1H,5H-octafluoropentanol, 1H,1H,7H-dodecafluoroheptanol, 1H,1H, 9H-hexadecafluorononanol; branched fluorine-containing alcohols such as 2-(perfluoro-3-methylbutyl)ethanol, 2-(perfluoro-5-methylhexyl)ethanol, 2-(perfluoro-7-methyloctyl)ethanol, 2-(perfluoro-9-methyldodecyl)ethanol, 6-(perfluoro-1-methylethyl)hexanol, 2-(perfluoro-3-methylbutyl)hexanol, 6-(perfluoro-5-methylhexyl)hexanol, 6-(perfluoro-7-methyloctyl)hexanol. Among these fluorine-containing compounds, 2-(perfluorohexyl)ethanol, 2-(perfluorooctyl)ethanol, 2-(perfluorodecyl)ethanol are preferred.

Carbonyl compounds represented by the general formula (3) include, in addition to compounds having carbonyl groups, compounds easily converted with acid or heating to those having carbonyl groups.

Carbonyl compounds represented by the general formula (3) used in the present invention include, but are not limited to, linear ketone such as acetone, methylethylketone, methylisobutylketone (4-methyl-2-pentanone), methyl-n-hexylketone, diethylketone, diisopropylketone; cyclic ketone such as cyclohexanone, 2-methylcyclohexanone, cyclopentanone, cycloheptanone; straight-chain aldehyde such as propionaldehyde, butyraldehyde, hexylaldehyde, octylaldehyde; branched aldehyde such as isobutyraldehyde, 2-ethylhexylaldehyde, isononyl aldehyde (3,5,5-trimethylhexanal).

Among these carbonyl compounds, $C_{6-9}$ linear ketone such as methylisobutylketone (4-methyl-2-pentanone); $C_{6-9}$ aliphatic aldehyde such as octylaldehyde, isononylaldehyde (3,5,5-trimethylhexanal), etc.; $C_{6-9}$ cyclic ketone such as cyclohexanone are particularly preferred, and further, methylisobutylketone (4-methyl-2-pentanone), octylaldehyde, isononylaldehyde (3,5,5-trimethylhexanal) are particularly preferred. In the above process, charge ratio of fluorine-containing hydroxy compound to carbonyl compound is not particularly limited, but generally the ratio of fluorine-containing compound/carbonyl compound (by mole) is preferably 30/1 to 1/30. Particularly, 20/1 to 1/20, especially, 10/1 to 1/10 is preferred. If the fluorine-containing hydroxy compound has a low molecular weight and can be easily removed, it is preferable to use such an excess of the fluorine-containing hydroxy compound as to react a carbonyl completely. If fluorine-containing hydroxy compound has high molecular weight and further solidifies at ambient temperature, it is preferable to use an excess of carbonyl compound to completely react fluorine-containing hydroxy compound which may be hardly removed. The molar ratio of fluorine-containing hydroxy compound/carbonyl compound out of the above range has little effect on yield, but is not economical.

In the present invention, catalysts used for reaction of a fluorine-containing hydroxy compound with a carbonyl compound may not be particularly limited so long as they have hydrogenation ability, and include palladium catalyst; palladium compound such as palladium hydroxide, palladium oxide; ruthenium, rhodium or platinum catalyst; ruthenium oxide, rhodium oxide, platinum oxide, etc. Catalysts such as iridium, osmium, rhenium may also be used. These catalysts may be appropriately supported on carriers such as carbon, alumina, silica alumina, silica and zeolite. Among these catalysts, preferably palladium compounds, more preferably palladium catalysts, palladium hydroxide or palladium oxide, which is supported on carbon, alumina, silica alumina, silica or zeolite, most preferably, palladium catalysts supported on carbon, can be used. In the present invention, catalysts may be generally used being supported on a carrier such as carbon, alumina at the ratio of 2 to 10% by weight, but they may be directly used instead of being supported on a carrier. Moreover, they may contain about 20 to 60% by weight of water.

Catalysts may be preferably used at 0.1 to 10% by weight based on fluorine-containing hydroxy compound or carbonyl compound to be used so long as they are those supported on a carrier at the ratio of 5% by weight based on the carrier. With less than 0.1% by weight of catalyst, reaction may proceed, but undesirably at slow rate. On the other hand, with more than 10% by weight of catalyst, reaction may proceed rapidly, but undesirably side reaction may proceed simultaneously. More preferably, the amount of catalyst is 0.5 to 5% by weight.

Catalysts may be used within any pH range, but preferably at pH 8 to 2, more preferably at pH 7.5 to 3. The term 'pH of catalyst' herein used means pH of an aqueous solution of catalyst powder (2 g) dispersed in ion exchanged water (30 g).

In the present invention, fluorine-containing compound and carbonyl compound are reacted in an atmosphere of hydrogen. The hydrogen pressure is not particularly limited, and the reaction may be carried out either at an increased pressure or at an atmospheric pressure, preferably at 1 (atmospheric pressure) to 300 kg/cm$^2$, particularly preferably at 1 (atmospheric pressure) to 200 kg/cm$^2$.

When carbonyl compounds are aldehydes, it is preferable to carry out reaction by adding such aldehydes dropwise to the reaction system. Reaction is carried out by adding aldehydes dropwise to the reaction system, which prevents side reaction (aldol formation) of aldehydes, yielding fluorine-containing ether compound at high yield. In addition, amount of aldehydes to be added may be reduced. The reaction can be completed generally with 1 to 2 times equivalent of aldehyde based on fluorine-containing hydroxyl compound.

The way to add aldehyde dropwise to the reaction system may not be particularly limited, but it is preferable to continuously and/or intermittently add dropwise to the reaction system within 0.5 to 20 hours. The rate to add aldehyde may be suitably selected depending on the reaction scale. For 0.5 liter scale, for example, 0.1 to 180 g/hr is preferred and 0.6 to 60 g/hr is more preferred.

In the present invention, reaction temperature during reaction between fluorine-containing compound and carbonyl compound is not particularly limited, but preferably 10 to 200° C., particularly preferably 30 to 180° C. The reaction time may be suitably selected depending on reaction temperature, hydrogen pressure, amount of catalyst, etc., and generally 1 to 24 hours, preferably 1 to 12 hours.

In the present reaction, the objective fluorine-containing ether compound as well as equimolar amount of water may be produced. It is preferable to carry out reaction while removing thus produced water, which preferably facilitates reaction. Examples of the method to remove water include, for example, to carry out reaction in the presence of a dehydrating agent to remove water, to flow gas such as hydrogen to remove water, to distill off water by azeotropic dehydration. Among them, the method is preferred wherein water is removed by carrying out reaction in the presence of a dehydrating agent or the method wherein water is removed using a flow of hydrogen. In particular, a method wherein water produced from the reaction as a by-product is removed from the system by flowing hydrogen using a reactor equipped with a dehydrating tube and only unreacted materials are recycled to the system.

In the method wherein reaction is carried out in the presence of a dehydrating agent, embodiments of such dehydrating agents used include anhydrous magnesium sulfate, anhydrous sodium sulfate, anhydrous calcium sulfate, anhydrous calcium chloride, molecular sieves, etc. Among them, anhydrous magnesium sulfate, anhydrous sodium sulfate are preferred, and anhydrous magnesium sulfate is most preferable. The amount of a dehydrating agent varies depending on types of the dehydrating agent to be used, and when anhydrous magnesium sulfate is used, 0.05 to 2 times mole, further 0.1 to 1 time mole based on the fluorine-containing hydroxy compound is preferred.

In the method wherein water is removed from the system with flowing hydrogen, the flow rate of hydrogen may be suitably selected depending on the reaction scale. For example 0.7 to 2100 ml/min. is preferable and 0.7 to 700 ml/min. is more preferable for 70 ml scale. Hydrogen may be flowed continuously or intermittently during the reaction, but continuous flow is preferred to smoothly conduct reaction. The hydrogen flowed through the reaction system may be directly released into air, but for efficient use of hydrogen, it is efficient and preferable to utilize the hydrogen released from the system for reaction by returning through a circulating line or the like and flowing again through the system and recycling again. Further, when unreacted materials are removed from the system simultaneously with water, it is preferable to return only unreacted materials to the system.

In the reaction according to the present invention, solvent which has no bad effect on the reaction may be sometimes used to carry out reaction. As such solvents having no bad effect on the reaction include, but are not limited to, hydrocarbon solvent such as hexane, heptane and octane.

When a solvent having no bad effect on the reaction is used, the amount of such a solvent to be used is not particularly limited, but preferably 0.5 to 2 times the volume of the reaction solution.

(Use)

The fluorine-containing ether compounds of the present invention have compatibility with hydrocarbon oil, ester oil, silicone oil, fluorine oil, etc., and have resistance to hydrolysis because they are ether compounds. Further, different from perfluoropolyethers which have been conventionally used for cosmetics, they have compatibility with organic solvents such as n-hexane, tetrahydrofuran, chloroform, acetone, ethanol, as well as functions corresponding to those of fluorine, thus they can be widely used as solvents, cosmetics, detergents, emulsifiers, surface finishing agents, lubricants, as well as lubricants or oils in the field of semiconductor/electronics.

The compound of the present invention is useful to solubilize and disperse a cosmetic preparation as a fluorinated oil or a fluorinated polymer.

The present invention provides a method for imparting a good compatibility with an organic solvent or oil to the above materials.

EXAMPLE

The present invention will be illustrated in detail in the following examples, but the present invention should not be construed to be limited to them.

Example 1

Production of 1,3-dimethylbutyl{2-(perfluorohexyl) ethyl}ether represented by the following formula (4):

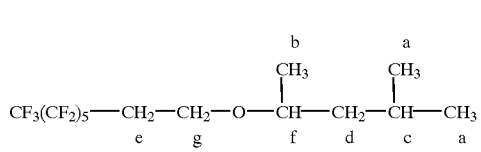

(4)

2-(Perfluorohexyl)ethanol 18.2 g (0.05 mol), 4-methyl-2-pentanone 30.0 g (0.3 mol), 5% Pd-C (pH 7.2) 1.5 g as a catalyst were charged in a 70 ml autoclave equipped with a hydrogen gas inlet and a stirrer, and stirring was continued at 105° C. for 10 hours while continuously flowing hydrogen at 18 ml/min. under atmospheric pressure.

After reaction was completed, catalyst was removed by filtration, and an excess of 4-methyl-2-pentanone was removed under reduced pressure. Further, after purification by silica gel column chromatography, the objective 1,3-dimethylbutyl{2-(perfluorohexyl)ethyl}ether 21.5 g (0.048 mol) was obtained as a colorless, transparent liquid. Isolation yield was 96%.

$^1$H-NMR($\delta$: ppm, CDCl$_3$)

0.90 (overlapping of two doublets, 6H: a)

1.15 (doublet, 3H: b)

1.10~1.25 (complicated multiplet, 1H: c)

1.30~1.85 (complicated multiplet, 2H: d)

2.20~2.50 (complicated multiplet, 2H: e)

3.40~3.60 (complicated multiplet, 1H: f)

3.55~3.90 (complicated multiplet, 2H: g)

b.p. 60~70° C./5Torr

IR C—H stretching vibration:2926, 2878 cm$^{-1}$

C—O—C stretching vibration:1083 cm$^{-1}$

CF$_3$ stretching vibration:1100~1340, 700~750 cm$^{-1}$

CF$_2$ stretching vibration:1146 cm$^{-1}$

Example 2

Production of 1,3-dimethylbutyl{2-(perfluorooctyl) ethyl}ether represented by the following formula (5):

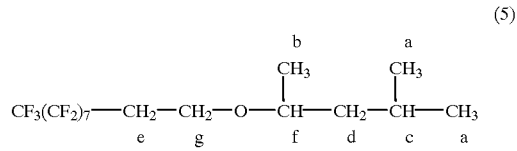

(5)

Hydroxy compound and carbonyl compound shown in Table 1 were reacted following the procedure of Example 1 in the presence of a catalyst shown in Table 1 under reaction conditions shown in Table 1, to provide the objective 1,3-dimethylbutyl{2-(perfluorooctyl)ethyl}ether 20.6 g (0.038 mol) as a colorless, transparent liquid. Isolation yield was 94%.

$^1$H-NMR($\delta$: ppm, CDCl$_3$)

0.90 (overlapping of two doublets, 6H: a)

1.15 (doublet, 3H: b)

1.10~1.25 (complicated multiplet, 1H: c)

1.30~1.85 (complicated multiplet, 2H: d)

2.20~2.50 (complicated multiplet, 2H: e)

3.40~3.60 (complicated multiplet, 1H: f)

3.55~3.90 (complicated multiplet, 2H: g)

b.p. 80~90° C./5Torr

IR C—H stretching vibration:2926, 2878 cm$^{-1}$

C—O—C stretching vibration:1110 cm$^{-1}$

CF$_3$ stretching vibration:1100~1340, 700~750 cm$^{-1}$

CF$_2$ stretching vibration:1152 cm$^{-1}$

Example 3

Production of octyl{2-(perfluorohexyl)ethyl}ether represented by the following formula (6):

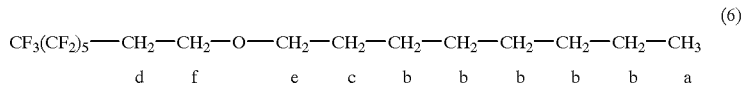
(6)

Hydroxy compound and carbonyl compound shown in Table 1 were reacted following the procedure of Example 1 in the presence of a catalyst shown in Table 1 under reaction conditions shown in Table 1, to provide the objective octyl{2-(perfluorohexyl)ethyl}ether 22.8 g (0.048 mol) as a colorless, transparent liquid. Isolation yield was 96%.

$^1$H-NMR($\delta$: ppm, CDCl$_3$)

0.87 (triplet, 3H: a)
1.15~1.45 (broad singlet, 10H: b)
1.45~1.70 (complicated multiplet, 2H: c)
2.23~2.55 (complicated multiplet, 2H: d)
3.45 (triplet, 2H: e)
3.70 (triplet, 2H: f)
b.p. 78~79° C./0.4Torr
IR C—H stretching vibration:2932, 2866 cm$^{-1}$
C—O—C stretching vibration:1089 cm$^{-1}$
CF$_3$ stretching vibration:1100~1340, 700~750 cm$^{-1}$
CF$_2$ stretching vibration:1146 cm$^{-1}$ Example 4

Production of octyl{2-(perfluorooctyl)ethyl}ether represented by the following formula (7):

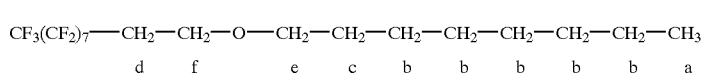
(7)

Hydroxy compound and carbonyl compound shown in Table 1 were reacted following the procedure of Example 1 in the presence of a catalyst shown in Table 1 under reaction conditions shown in Table 1, to provide the objective octyl{2-(perfluorooctyl)ethyl}ether 22.6 g (0.039 mol) as a colorless, transparent liquid. Isolation yield was 98%.

$^1$H-NMR($\delta$: ppm, CDCl$_3$)

0.90 (triplet, 3H: a)
1.15~1.45 (broad singlet, 10H: b)
1.45~1.70 (complicated multiplet, 2H: c)
2.20~2.55 (complicated multiplet, 2H: d)
3.45 (triplet, 2H: e)
3.70 (triplet, 2H: f)
b.p. 98° C./0.4Torr
IR C—H stretching vibration:2932, 2866 cm$^{-1}$
C—O—C stretching vibration:1120 cm$^{-1}$
CF$_3$ stretching vibration:1100~1340, 700~750 cm$^{-1}$
CF$_2$ stretching vibration:1149 cm$^{-1}$ Example 5

Production of octyl{2-(perfluorodecyl)ethyl}ether represented by the following formula (8):

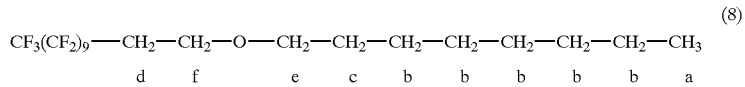
(8)

Hydroxy compound and carbonyl compound shown in Table 1 were reacted following the procedure of Example 1 in the presence of a catalyst shown in Table 1 under reaction conditions shown in Table 1, yielding the objective octyl{2-(perfluorodecyl)ethyl}ether 23.2 g (0.034 mol) as a colorless, transparent liquid. Isolation yield was 98%.

$^1$H-MMR ($\delta$: ppm, CDCl$_3$)

0.90 (triplet, 3H: a)
1.15~1.47 (broad singlet, 10H: b)
1.47~1.75 (complicated multiplet, 2H: c)
2.25~2.60 (complicated multiplet, 2H: d)
3.47 (triplet, 2H: e)
3.72 (triplet, 2H: f)
b.p. 115~117° C./0.3Torr
m.p. 30° C.
IR C—H stretching vibration:2932, 2866 cm$^{-1}$
C—O—C stretching vibration:1130 cm$^{-1}$
CF$_3$ stretching vibration:1100~1340, 700~750 cm$^{-1}$
CF$_2$ stretching vibration:1152 cm$^{-1}$

TABLE 1

| Ex | Hydroxy compound | Carbonyl compound | Catalyst | Reaction condition |
|---|---|---|---|---|
| 2 | 2-(perfluorooctyl) ethanol 18.6 g (0.04 mol) | 4-methyl-2-pentanone 24.0 g (0.24 mol) | 5% Pd-C (pH 6.8) 0.7 g | 150° C. H$_2$ pressure 1.5 kg/cm$^2$ H$_2$ flow amount 18 ml/min 11 hr. |
| 3 | 2-(perfluorohexyl) ethanol 18.2 g (0.05 mol) | Octylaldehyde 9.6 g (0.075 mol) added dropwise for 6 hours * | 5% Pd-C (pH 7.2) 1.5 g | 105° C. H$_2$ pressure atmospheric pressure H$_2$ flow amount 15 ml/min 8 hr. |

TABLE 1-continued

| Ex | Hydroxy compound | Carbonyl compound | Catalyst | Reaction condition |
|---|---|---|---|---|
| 4 | 2-(perfluorooctyl)ethanol 18.6 g (0.04 mol) | Octylaldehyde 7.7 g (0.06 mol) added dropwise for 6 hours * | 5% Pd-C (pH 6.8) 1.5 g | 120° C. $H_2$ pressure atmospheric pressure $H_2$ flow amount 15 ml/min 8 hr. |
| 5 | 2-(perfluorodecyl)ethanol 19.7 g (0.035 mol) | Octylaldehyde 8.96 g (0.07 mol) added dropwise for 6 hours * | 5% Pd-C (pH 7.2) 1.6 g | 150° C. $H_2$ pressure atmospheric pressure $H_2$ flow amount 15 ml/min 8 hr. |

*: The carbonyl compound was added dropwise under the above conditions after the hydroxy compound and the catalyst has been added.

Example 6

Production of 3,5,5-trimethylhexyl{2-(perfluorohexyl)ethyl}ether represented by the following formula (9):

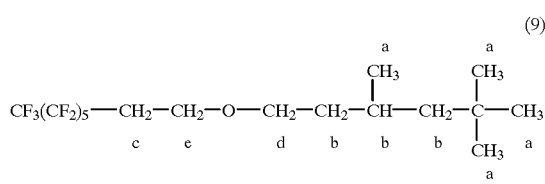

(9)

2-(Perfluorohexyl)ethanol 18.2 g (0.05 mol), 5% Pd-C (pH 7.2) 1.5 g as a catalyst were charged in a 70 ml autoclave equipped with a hydrogen gas inlet and a stirrer, to which was added dropwise 3,5,5-trimethylhexanal-(isononylaldehyde) 10.7 g (0.075 mol) under atmospheric pressure over 6 hours, and stirring was continued at 150° C. for 8 hours with continuously flowing hydrogen at 15 ml/min. After reaction was completed, catalyst was removed by filtration, and an excess of 3,5,5-trimethylhexanal was removed under reduced pressure to provide the objective 3,5,5-trimethylhexyl{2-(perfluorohexyl)ethyl}ether 23.3 g (0.048 mol) as a colorless, transparent liquid. Isolation yield was 95%.

$^1$H-NMR($\delta$: ppm, $CDCl_3$)

0.25~0.90 (overlapping of singlet and doublet, 12H: a)
0.90~1.65 (complicated multiplet, 5H: b)
2.10~2.50 (complicated multiplet, 2H: c)
3.40 (triplet, 2H: d)
3.62 (triplet, 2H: e)
b.p. 75° C./2Torr
IR C—H stretching vibration:2956, 2902 $cm^{-1}$
C—O—C stretching vibration:1110 $cm^{-1}$
$CF_3$ stretching vibration:1080~1340, 700~770 $cm^{-1}$
$CF_2$ stretching vibration:1146 $cm^{-1}$

Example 7

Production of 3,5,5-trimethylhexyl{2-(perfluorooctyl)ethyl}ether represented by the following formula (10):

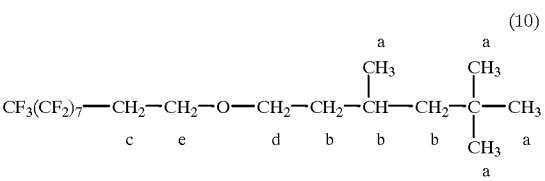

(10)

The procedure of Example 6 was repeated, except that 2-(perfluorooctyl)ethanol 18.6 g (0.04 mol) was used instead of 2-(perfluorohexyl)ethanol and amount of 3,5,5-trimethylhexanal to be added was changed to 8.5 g (0.06 mol), yielding the objective 3,5,5-trimethylhexyl{2-perfluorooctyl)ethyl}ether 22.4 g (0.038 mol) as a colorless, transparent liquid. Isolation yield was 95%.

$^1$H-NMR($\delta$: ppm, $CDCl_3$)

0.23~0.90 (overlapping of singlet and doublet, 12H: a)
0.90~1.65 (complicated multiplet, 5H: b)
2.10~2.50 (complicated multiplet, 2H: c)
3.40 (triplet, 2H: d)
3.62 (triplet, 2H: e)
b.p. 9~3° C./2Torr
IR C—H stretching vibration 2956, 2878 $cm^{-1}$
C—O—C stretching vibration:1130 $cm^{-1}$
$CF_3$ stretching vibration:1100~1340, 700~760 $cm^{-1}$
$CF_2$ stretching vibration:1152 $cm^{-1}$ Physical properties data of the compounds described in the above Examples 1 to 7 are shown in the following Table 2.

The compatibility was determined by preparing a mixture of the compound of the present invention and a liquid medium (solvent) at the concentration of 10% by weight of the compound of the present invention, as shown in Table 2, and observing the appearance. S means "being soluble" and I means "being insoluble" in which two phases are seen to be separated. In Table 2, the ester oil is Estemol N-01 (trade name of Nisshin Oil Mills), the silicone oil is SH200C-6cs (trade name of Toray Dow Corning Silicone) and the fluorine oil is Fomblin HC-04 (trde name of Ausimont).

TABLE 2

| | Structure | MW | State | n-hexane | THF | CHCl$_3$ | acetone | EtOH | H$_2$O | Ester Oil (Estemol N-01) | Silicone Oil (SH200C-6cs) | Fluorine Oil (Fomblin HC-04) |
|---|---|---|---|---|---|---|---|---|---|---|---|---|
| Ex. 1 | C$_6$F$_{13}$–O–(isobutyl) | 448 | Oil | S | S | S | S | S | I | S | S | S |
| Ex. 2 | C$_8$F$_{17}$–O–(isobutyl) | 548 | Oil | S | S | S | S | S | I | S | S | S |
| Ex. 3 | C$_6$F$_{13}$–O–(n-alkyl) | 476 | Oil | S | S | S | S | S | I | S | S | I |
| Ex. 4 | C$_8$F$_{17}$–O–(n-alkyl) | 576 | Oil | S | S | S | S | S | I | S | S | I |
| Ex. 5 | C$_{10}$F$_{21}$–O–(n-alkyl) | 676 | Wax | S | S | S | S | S | I | S | S | S |
| Ex. 6 | C$_6$F$_{13}$–O–(branched) | 490 | Oil | S | S | S | S | S | I | S | S | S |
| Ex. 7 | C$_8$F$_{17}$–O–(branched) | 590 | Oil | S | S | S | S | S | I | S | S | S |
| Comp. compd. Fomblin HC-04 | CF$_3$O(CFCF$_2$O)n(CF$_2$O)mCF$_3$ with CF$_3$ branch | 1500 | Oil | I | I | I | I | I | I | I | I | — |

What is claimed is:

1. A fluorine-containing ether compound represented by the formula (1):

$$Rf-(CH_2)_n-O-R^1 \quad (1)$$

wherein Rf represents a straight or branched $C_{1-20}$ perfluoroalkyl or fluoroalkyl group, $R^1$ is a straight or branched $C_{3-9}$ alkyl or a $C_{3-9}$ cycloalkyl group, n is a number from 1 to 8.

2. A fluorine-containing ether compound according to claim 1, wherein Rf contains 2 to 14 carbon atoms and n is a number from 1 to 6.

3. A fluorine-containing ether compound according to claim 1, wherein Rf contains 4 to 12 carbon atoms and n is a number from 1 to 4.

4. A fluorine-containing ether compound according to claim 1, wherein n is 2.

5. A fluorine-containing ether compound according to claim 1, wherein $R^1$ is a straight or branched $C_{6-9}$ alkyl group.

6. A fluorine-containing ether compound according to claim 1, wherein $R^1$ is a branched $C_{6-9}$ alkyl group.

7. An composition which comprises a compound according to claim 1 and an organic solvent or oil which is different from said compound.

8. A process for production of a fluorine-containing ether compound defined in claim 1, which comprises reacting a hydroxy compound, $Rf-(CH_2)_n-OH$, and a carbonyl compound, $R^2-(C=O)-R^3$, in the presence of a catalyst in an atmosphere of hydrogen to obtain the ether compound, wherein $R^2$ and $R^3$ are the same or different and each is a hydrogen atom or a $C_{1-9}$ alkyl group, or $R^2$ and $R^3$ together form a ring, provided that the total number of carbon atoms of $R^2$ and $R^3$ together is 2 to 8.

9. A process according to claim 8, wherein catalyst is selected from the group consisting of palladium, palladium hydroxide and palladium oxide supported on carbon, alumina, silica alumina, silica, or zeolite.

10. A process according to claim 8, wherein the reaction is carried out while removing water which has been produced as a by-product during the reaction.

11. A fluorine-containing ether compound according to claim 1, selected from the group consisting of 1,3-dimethylbutyl{2-(perfluorohexyl)ethyl}ether, 1,3-dimethylbutyl{2-(perfluorooctyl)ethyl}ether, octyl{2-(perfluorohexyl)ethyl}ether, octyl{2-(perfluorooctyl)ethyl}ether, octyl{2-perfluorodecyl)ethyl } ether, 3,5,5-trimethylbexyl{2-(perfluorohexyl)ethyl}ether and 3,5,5-trimethylhexyl{2-(perfluorooctyl)ethyl}ether.

* * * * *